United States Patent
Cabiri et al.

(10) Patent No.: US 11,116,908 B2
(45) Date of Patent: Sep. 14, 2021

(54) BENT FLUID PATH ADD ON TO A PREFILLED FLUID RESERVOIR

(71) Applicant: West Pharma. Services IL, Ltd., Ra'anana (IL)

(72) Inventors: Oz Cabiri, Macabim-Reut (IL); Paul H. Norton, St. Augustine, FL (US); Ran Hezkiahu, Herzliya (IL); Richard Brough, Scottsdale, AZ (US)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 485 days.

(21) Appl. No.: 15/766,719

(22) PCT Filed: Oct. 10, 2016

(86) PCT No.: PCT/US2016/056213
§ 371 (c)(1),
(2) Date: Apr. 6, 2018

(87) PCT Pub. No.: WO2017/062931
PCT Pub. Date: Apr. 13, 2017

(65) Prior Publication Data
US 2018/0318511 A1    Nov. 8, 2018

Related U.S. Application Data

(63) Continuation of application No. 15/269,248, filed on Sep. 19, 2016, now Pat. No. 10,086,145, and a (Continued)

(51) Int. Cl.
*A61M 5/28* (2006.01)
*A61M 5/32* (2006.01)
(Continued)

(52) U.S. Cl.
CPC ............ *A61M 5/28* (2013.01); *A61M 5/3134* (2013.01); *A61M 5/3202* (2013.01); (Continued)

(58) Field of Classification Search
CPC ........... A61M 2005/14252; A61M 2005/1426; A61M 2005/14256; A61M 2005/1581; A61M 2005/1585; A61M 2005/3132
See application file for complete search history.

(56) References Cited

U.S. PATENT DOCUMENTS

| | | | |
|---|---|---|---|
| 1,125,887 A | 1/1915 | Schimmel | |
| 1,321,550 A | 11/1919 | Platt | |

(Continued)

FOREIGN PATENT DOCUMENTS

| | | |
|---|---|---|
| DE | 855313 C | 11/1952 |
| EP | 2364739 A1 | 9/2011 |

(Continued)

OTHER PUBLICATIONS

Int'l Search Report and Written Opinion dated Jan. 26, 2017 in Int'l Application No. PCT/US2016/056213.
(Continued)

*Primary Examiner* — Nathan R Price
*Assistant Examiner* — Tasnim Mehjabin Ahmed
(74) *Attorney, Agent, or Firm* — Panitch Schwarze Belisario & Nadel LLP

(57) ABSTRACT

An add-on for a self-injector including an adaptor and a bent fluid path is provided. The adaptor includes at least one coupling sized and shaped to couple the adaptor to a fluid reservoir. The bent fluid path is configured at a first end to penetrate tissue and coupled at a second end to the adaptor. The add-on coupled to the fluid reservoir forms an integral self-injector cartridge unit configured to be sterilized and filled with an injectable. The adaptor is configured to couple
(Continued)

to a self-injector at least one of a plurality of reservoirs having different sizes and tip types.

33 Claims, 7 Drawing Sheets

Related U.S. Application Data continuation of application No. 15/204,542, filed on Jul. 7, 2016, now Pat. No. 10,576,207.

(60) Provisional application No. 62/281,536, filed on Jan. 21, 2016, provisional application No. 62/284,806, filed on Oct. 9, 2015.

(51) Int. Cl.
| | | |
|---|---|---|
| A61M 5/142 | (2006.01) | |
| A61M 5/158 | (2006.01) | |
| A61M 5/31 | (2006.01) | |
| A61M 5/34 | (2006.01) | |
| B65D 1/36 | (2006.01) | |
| B65D 25/10 | (2006.01) | |
| B65D 5/50 | (2006.01) | |
| B65D 21/02 | (2006.01) | |
| A61M 5/145 | (2006.01) | |

(52) U.S. Cl.
CPC ............ *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(56) References Cited

U.S. PATENT DOCUMENTS

| 4,710,178 | A | 12/1987 | Henri et al. | |
|---|---|---|---|---|
| 4,861,341 | A * | 8/1989 | Woodburn | A61M 5/158 |
| | | | | 604/175 |
| 5,275,582 | A | 1/1994 | Wimmer | |
| 5,858,001 | A * | 1/1999 | Tsais | A61M 5/1454 |
| | | | | 604/135 |
| 6,189,292 | B1 | 2/2001 | Odell et al. | |
| 6,500,150 | B1 * | 12/2002 | Gross | A61M 5/14248 |
| | | | | 604/110 |
| 6,685,678 | B2 * | 2/2004 | Evans | A61M 5/31533 |
| | | | | 604/207 |
| 6,719,141 | B2 | 4/2004 | Heinz et al. | |
| 6,824,529 | B2 | 11/2004 | Gross et al. | |
| 6,843,782 | B2 | 1/2005 | Gross et al. | |
| 7,967,795 | B1 | 6/2011 | Cabiri | |
| 8,496,862 | B2 | 7/2013 | Zelkovich et al. | |
| 8,603,028 | B2 | 12/2013 | Mudd et al. | |
| 8,721,603 | B2 | 5/2014 | Lundquist | |
| 9,468,720 | B2 * | 10/2016 | Mudd | A61M 5/20 |
| 2002/0055718 | A1 * | 5/2002 | Hunt | A61M 39/12 |
| | | | | 604/198 |
| 2005/0154353 | A1 | 7/2005 | Alheidt | |
| 2007/0079894 | A1 * | 4/2007 | Kraus | A61J 1/201 |
| | | | | 141/319 |
| 2008/0140014 | A1 * | 6/2008 | Miller | A61M 39/0247 |
| | | | | 604/180 |
| 2009/0093792 | A1 | 4/2009 | Gross et al. | |
| 2013/0131589 | A1 | 5/2013 | Mudd et al. | |
| 2013/0253434 | A1 | 9/2013 | Cabiri | |
| 2014/0163526 | A1 | 6/2014 | Cabiri et al. | |
| 2015/0112278 | A1 | 4/2015 | Ray et al. | |
| 2015/0157806 | A1 | 6/2015 | Knutsson | |

FOREIGN PATENT DOCUMENTS

| EP | 2452708 A1 | 5/2012 |
|---|---|---|
| JP | 2007306990 A | 11/2007 |
| JP | 2009101093 A | 5/2009 |
| JP | 2014030489 A | 2/2014 |
| WO | 9721457 A1 | 6/1997 |
| WO | 200170304 A1 | 9/2001 |
| WO | 2005070485 A1 | 8/2005 |
| WO | 2009043000 A1 | 4/2009 |
| WO | 2011110872 A1 | 9/2011 |
| WO | 2011129175 A1 | 10/2011 |
| WO | 2013036602 A1 | 3/2013 |
| WO | 2014132293 A1 | 9/2014 |
| WO | 2015114428 A1 | 8/2015 |

OTHER PUBLICATIONS

Int'l Preliminary Report on Patentability dated Jan. 18, 2018 in Int'l Application No. PCT/US2016/056213.
Office Action dated Oct. 13, 2020 in Japanese Application No. 2018-538073.
Office Action dated May 25, 2021 in Japanese Office Action 2018-538073.

* cited by examiner

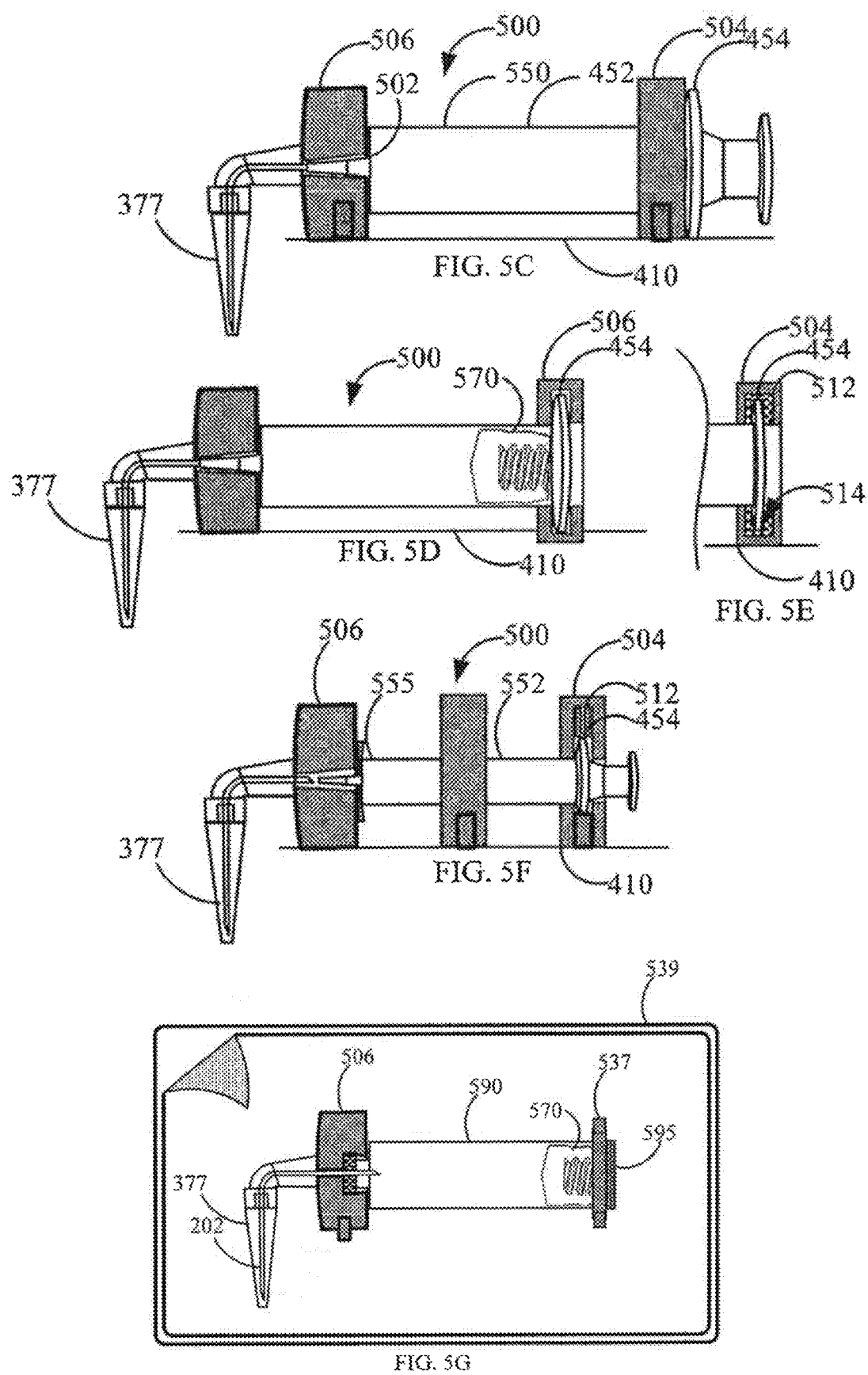

BENT FLUID PATH ADD ON TO A PREFILLED FLUID RESERVOIR

CROSS REFERENCE TO RELATED APPLICATION

This application is a section 371 of International Application No. PCT/US16/56213, filed Oct. 10, 2016, which was published Apr. 13, 2017 under International Publication No. WO 2017/062931 A1, which is a continuation of U.S. application Ser. No. 15/204,542, filed Jul. 7, 2016, which claims the benefit of U.S. Provisional Application No. 62/281,536, filed Jan. 21, 2016 and U.S. Provisional Application No. 62/284,806, filed Oct. 9, 2015; and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to a self-injector and, more particularly, but not exclusively, to a patch self-injector.

A subcutaneous (SC) injection is a method of administering medication under the skin, commonly into fatty tissue between the skin and the muscle. The current trend toward subcutaneous injection for biologicals using auto-injectors such as, for example, reusable and disposable pens, auto-injectors, and patch injectors that adhere to the surface of the skin gives users the freedom to self-inject at home.

In many cases, reformulated drugs can be more concentrated, at times more viscous and the desired injection volume greater than 1 mL. For high viscosity products, delivery in under 10 seconds can lead to painful injections, which may result in users failing to follow their treatment regimen. It may be difficult at times for a user to keep a Pen or any other upright injector stationary and at a correct angle of injection during injections for periods of over 10 seconds or several minutes. Patch auto or self-injectors for self-administered SC injections are therefore becoming more common.

Additional background art includes U.S. Pat. Nos. 6,843,782 and 5,858,001.

SUMMARY OF THE INVENTION

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein the add-on coupled to the fluid reservoir forms an integral self-injector cartridge unit configured to be sterilized and filled with an injectable.

According to some embodiments of the invention, the add-on includes a needle protective cap. According to some embodiments the fluid path is bent at a 90 degree angle. According to some embodiments, the add-on further includes at least one fastener sized and fitted to couple the body of the reservoir to a self-injector.

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein when the add-on is coupled to the fluid reservoir sterile fluid communication is secured between the reservoir and the first end of the bent fluid path. According to some embodiments of the invention, the bent fluid path includes a coupling at the second end sized and shaped to couple the bent fluid path to the adaptor and secure sterile fluid communication in-between. According to some embodiments of the invention, the add-on further includes at least one fastener sized and fitted to couple the body of the reservoir to a self-injector. According to some embodiments of the invention, the bent fluid path includes a hollow needle. According to some embodiments of the invention, the fluid path is bent at a 90 degree angle.

According to some embodiments of the invention, the reservoir is a prefilled cartridge. According to some embodiments of the invention, the reservoir is a syringe. According to some embodiments of the invention, the reservoir is a vial. According to some embodiments of the invention, at least a portion of the reservoir is made of glass. According to some embodiments of the invention, at least a portion of the reservoir is made of a plastic material. According to some embodiments of the invention, the add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on for a self-injector, including at least one adaptor including at least one bent fluid path and sized and fitted to sterilely couple the bent fluid path to at least a tip of a fluid reservoir, and at least one fastener sized and fitted to a body of the fluid reservoir to the self-injector, and wherein the adaptor and the fastener are configured to couple to the self-injector at least one of a plurality of reservoirs having different sizes and tip types.

According to some embodiments of the invention, the distance between the adaptor and the fastener is adjustable. According to some embodiments of the invention, the internal diameter of the fastener is adjustable. According to some embodiments of the invention, the add-on further includes a fitting sized and shaped to fit along the inner circumference of the fastener. According to some embodiments of the invention, the fitting reduces the inner diameter of the fastener. According to some embodiments of the invention, at least a portion of the fastener is made of a plastic material. According to some embodiments of the invention, at least a portion of the fluid reservoir is made of glass. According to some embodiments of the invention, at least a portion of the fluid reservoir is made of a plastic material. According to some embodiments of the invention, the bent fluid path includes a hollow needle. According to some embodiments of the invention, the fluid path is bent at a 90 degree angle.

According to some embodiments of the invention, the reservoir is a prefilled cartridge. According to some embodiments of the invention, the reservoir is a fluid reservoir. According to some embodiments of the invention, the reservoir is a vial. According to some embodiments of the invention, add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on to a self-injector coupling system, including a self-injector including a support plate with a plurality of attachment points, at least one adaptor including at least one bent fluid path and sized and fitted to sterilely couple the bent fluid path to at least a tip of a fluid reservoir and at least one fastener sized and fitted to couple to a body of the fluid reservoir and to at least one of the attachment points.

According to some embodiments of the invention, the adaptor is sized and fitted to couple to at least one of the attachment points. According to some embodiments of the invention, the attachment points are distributed on the support plate at varying distances from the adaptor. According to some embodiments of the invention, the varying distances correspond to varying lengths of the fluid reservoir. According to some embodiments of the invention, the internal diameter of the fastener is adjustable. According to some embodiments of the invention, the system further includes a fitting sized and shaped to fit along the inner circumference of the fastener. According to some embodiments of the invention, the fitting reduces the inner diameter of the fastener.

According to an aspect of some embodiments of the present invention there is provided a self-injector kit, including at least one self-injector including a support plate with a plurality of attachment points, a plurality of adaptors including at least one bent fluid path and sized and fitted to sterilely couple the bent fluid path to at least a tip of at least one type of fluid reservoir and a plurality of fasteners sized and fitted to couple to at least one diameter of a body of the fluid reservoir and to at least one of the attachment points.

According to some embodiments of the invention, at least one fitting is sized and shaped to fit along the inner circumference of at least one of the plurality of fasteners. According to some embodiments of the invention, the fitting reduces the inner diameter of the fastener. According to some embodiments of the invention, the fluid reservoir is at least one of a prefilled cartridge, a syringe and a vial. According to some embodiments of the invention, at least a portion of the fluid reservoir is made of glass. According to some embodiments of the invention, at least a portion of the fastener is made of a plastic material. According to some embodiments of the invention, at least one of the adaptors is sterile.

According to an aspect of some embodiments of the present invention there is provided a method of assembling an add-on for a self-injector including: selecting an empty fluid reservoir, forming a self-injector cartridge unit by coupling at least a tip of the fluid reservoir to an adaptor including at least one bent fluid path and sized and fitted to fluidly couple the bent fluid path to at least a tip of the fluid reservoir and establishing fluid communication between the fluid reservoir and the bent fluid path.

According to some embodiments of the invention, the method further includes sterilizing the cartridge, filling the fluid reservoir with a sterile injectable, inserting a plunger into a non-bent fluid path end of the fluid reservoir and sterilely sealing the end of the fluid reservoir. According to some embodiments of the invention, the method further includes selecting at least one fastener and coupling the fastener to a body of the fluid reservoir and coupling the fastener to at least one corresponding attachment point on the injector.

According to an aspect of some embodiments of the present invention there is provided a method of coupling an add-on for a self-injector to a fluid reservoir including: selecting a fluid reservoir, coupling at least a tip of the fluid reservoir to an adaptor including at least one bent fluid path and sized and fitted to fluidly couple the bent fluid path to at least a tip of the fluid reservoir and establishing sterile communication between the fluid reservoir and the bent fluid path.

According to some embodiments of the invention, the method further includes selecting at least one fastener and coupling the fastener to a body of the fluid reservoir and coupling the fastener to at least one corresponding attachment point on the injector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5A, 5B, 5C, 5D, 5E, 5F and 5G are part sectional side view simplified illustrations of positioning of fasteners coupling a fluid reservoir to a self-injector.

DESCRIPTION OF SPECIFIC EMBODIMENTS OF THE INVENTION

Figure 1:
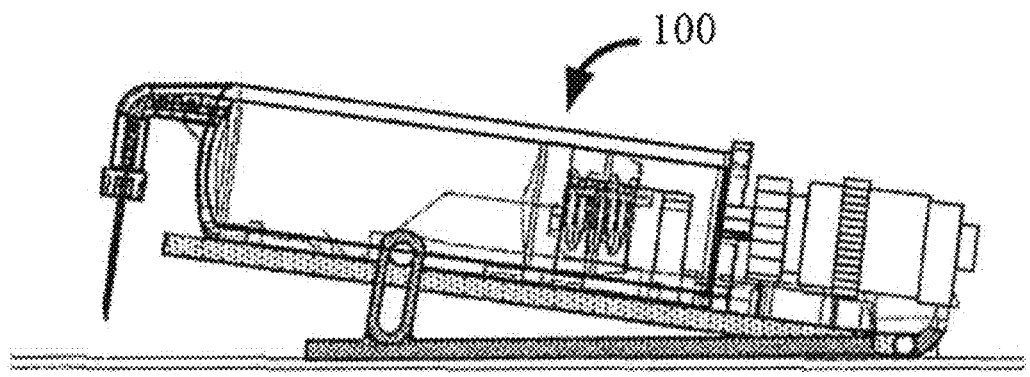
FIG. 1 is a side view simplified illustration of a patch type self-injector.

The present invention, in some embodiments thereof, relates to self-injectors and, more particularly, but not exclusively, to a patch self-injector.

An aspect of some embodiments of the invention relates to a self-injector sized and fitted to couple fluid reservoirs of variable sizes and tip types to the injector. In some embodiments, the self-injector comprises at least a needle-bearing portion and at least one fastener attachable to the injector and at least to a barrel of a fluid reservoir. In some embodiments, the needle bearing portion comprises a needle protective cap. In some embodiments, the self-injector and the fluid reservoir are provided sterile. For example, the reservoir, needle bearing portion and cap may be assembled and sterilized together. In some embodiments, the self-injector and the fluid reservoir are provided unsterile. In some embodiments, the self-injector and the fluid reservoir are sterilized prior to filling with an injectable. In some embodiments, post sterilization the sterile fluid reservoir is filled with an injectable and provided sterilely sealed and capped with a protective cap. In some embodiments, the distance between the needle-bearing portion and the fastener is adjustable. In some embodiments, the internal radius of the fastener is adjustable. In some embodiments, the injector comprises a patch type self-injector. In some embodiments, the injector comprises a bent needle. In some embodiments, the needle is bent at a 90 degree angle. In some embodiments, at least one portion of the injector comprises at least a bore sized and fitted to accommodate a fluid reservoir tip. In some embodiments, at least a portion of the needle extends through the bore. In some embodiments, the needle-bearing portion is fixed in place. In some embodiments the fluid reservoir comprises a syringe. In some embodiments, the fluid reservoir comprises a vial. In some embodiments the fluid reservoir comprises a prefilled cartridge.

In some embodiments, the self-injector is sized and fitted to accommodate refillable fluid reservoirs. In some embodiments, a self-injector is sized and fitted to accommodate prefilled fluid reservoirs. In some embodiments the prefilled fluid reservoir tips are sealed for sterility. In some embodiments, the injector comprises one or more adaptors that couple the needle to one or more fluid reservoir tip types. In some embodiments, the adaptor is sized and fitted for coupling the needle to a slip or push-on type fluid reservoir tip. In some embodiments, the adaptor is sized and fitted for coupling the needle to a Luer-lock type fluid reservoir tip. In some embodiments, the adaptor is sized and fitted for coupling the needle to a catheter type fluid reservoir tip. In some embodiments, the adaptor is sized and fitted for coupling the needle to a fluid reservoir with a centered tip. In some embodiments, the adaptor is sized and fitted for coupling the needle to a fluid reservoir with an eccentric tip.

An aspect of some embodiments of the invention relates to a self-injector comprising a modular fluid reservoir-injector coupling system. In some embodiments, the modular system comprises a support plate sized and fitted to accommodate variable types and sizes of fluid reservoirs. In some embodiments, the injector comprises a bent needle. In some embodiments, the needle is bent at a 90 degree angle. In some embodiments, the support plater comprises one or more notches configured to accommodate fasteners that fix the fluid reservoir to the injector. In some embodiments, at least a portion of one or more fasteners is fixedly coupled to a self-injector support plate. In some embodiments, at least a portion of one or more fasteners is releasably coupled to the self-injector support plate. In some embodiments, one or more fasteners comprises at least an aperture sized and fitted to accommodate a fluid reservoir tip. In some embodiments, at least one fastener comprises a bent needle. In some embodiments, at least one fastener comprises at least a bore sized and fitted to accommodate a fluid reservoir tip. In some embodiments, at least a portion of the needle extends through the aperture or bore.

In some embodiments, at least one fastener comprises a latch and a hinge. In some embodiments, at least one fastener comprises one or more latches. In some embodiments, at least one fastener is sized and fitted to fasten a barrel of a fluid reservoir. In some embodiments, at least one fastener is sized and fitted to fasten a finger flange of a fluid reservoir. In some embodiments, at least one fastener comprises at least one fitting sized and fitted for a specific fluid reservoir barrel diameter. In some embodiments, at least one fastener is fitted with an at least partially resilient pad. In some embodiments, at least a portion of a fluid reservoir is urged against the resilient pad when locked into place in the injector. In some embodiments, the resilient pad stops leaks from the fluid reservoir tip-needle coupling. In some embodiments, the resilient pad comprises an aperture for a tip of a needle.

An aspect of some embodiments of the invention relates to a self-injector comprising a bent needle and having a Luer-lock coupling sized and fitted to receive a fluid reservoir with a male Luer-lock type tip. In some embodiments, the Luer-lock coupling comprises a cylinder coupled at one end to the injector and comprising a tabbed rim configured to screw into a male Leur-lock fluid reservoir tip. In some embodiments, at least a portion of the bent needle is disposed in a lumen of the cylinder. In some embodiments, at least a portion of the needle is attached to the inside wall of the cylinder. In some embodiments, at least a portion of the cylinder lumen between the portion of the needle and the inside wall comprises a seal. In some embodiments, at least one end of the bent needle extends beyond the cylinder tabbed rim. In some embodiments, the end of the bent needle extending beyond the cylinder tabbed rim comprises a protective sheath. In some embodiments, the protective sheath maintains sterility of the needle end. In some embodiments, the protective sheath maintains sterility of the portion of the needle inside the cylinder lumen up to and including the end of the needle extending beyond the tabbed rim. In some embodiments, upon coupling, the rim of the male luer lock urges the protective sheath against the tip of the needle. In some embodiments, the needle tip ruptures the protective sheath urged against the needle tip by the male luer lock rim.

An aspect of some embodiments of the invention relates to a self-injector sized and fitted to sterilely accommodate variable types and sizes of fluid reservoirs. In some embodiments, the self-injector comprises a coupling that maintains sterility of a pathway of an injectable during and after coupling to a fluid reservoir containing the injectable. In some embodiments, the injector coupling comprises an end of a needle at least partially isolated by at least one protective sheath. In some embodiments, during coupling a tip of a coupled fluid reservoir urges at least one sheath against the needle end rupturing the protective sheath. In some embodiments, a tip of a coupled fluid reservoir comprises a sealing membrane over an opening in the tip. In some embodiments, during coupling the injector needle is urged against the membrane and penetrates the fluid reservoir tip.

An aspect of some embodiments of the invention relates to a self-injector kit comprising a support plate and a plurality of fasteners and fittings sized and fitted to attach to the support plate. In some embodiments, the plurality of fasteners and fittings sized and fitted to sterilely accommodate variable types and sizes of fluid reservoirs. In some embodiments, the plurality of fasteners comprises quick attachment type coupling. In some embodiments, the plurality of fasteners comprises at least one one-click type coupling. In some embodiments, various fasteners can be coupled to the support place at various desired locations. In some embodiments, at least one fastener comprises a bent needle. In some embodiments, one or more fasteners are configured to accommodate at least one fitting. In some embodiments, one or more fasteners and/or fittings comprise one or more apertures at various internal diameters to fit at least one barrel and/or finger flange of at least one fluid reservoir.

An aspect of some embodiments of the invention relates to a method of loading variable types and sizes of fluid reservoirs a self-injector. In some embodiments, the method comprises one or more fasteners sized and fitted for a barrel and finger flange of a selected fluid reservoir. In some embodiments, the method comprises optionally, selecting at least one fitting sized and fitted for a barrel and finger flange of a selected fluid reservoir. In some embodiments, the method further comprises optionally sliding or coupling one or more fittings onto the barrel or finger flange of the fluid reservoir. In some embodiments, the method further comprises sliding or coupling one or more fasteners onto the barrel or finger flange of the fluid reservoir. In some embodiments, the method further comprises inserting a tip of a fluid reservoir into an aperture in a needle portion of the injector. In some embodiments, the method further comprises optionally inserting a tip of a fluid reservoir into an aperture in a needle-bearing fastener. In some embodiments, the method further comprises coupling the fasteners to a support plate. In some embodiments, the method further comprises connecting the fluid reservoir to a injector fluid reservoir plunger driving system.

Introduction

Reference is now made to FIG. 1, which is a side view simplified illustration of a patch type self-injector as described in U.S. Provisional Patent Application 62/284,806 and is hereby incorporated in its entirety. Self-injector 100 comprises a bent needle 102, e.g., bent at a 90 degree angle coupled to a cartridge 104. Cartridge 104 may be pre-filled with an injectable. Cartridge 104 may be mounted on a support plate 106 and include a plunger 108 driven by electric motor driving gear 110. Following an injection procedure, cartridge 104 may be disposed of and replaced by a new pre-filled cartridge.

The injector powertrain and plunger driving systems are explained in detail in the above referenced U.S. Provisional Patent Application 62/284,806 and will therefore not be repeated herein.

Optional Components of a Modular Self-Injector-Fluid Reservoir Coupling System.

Figure 2A:
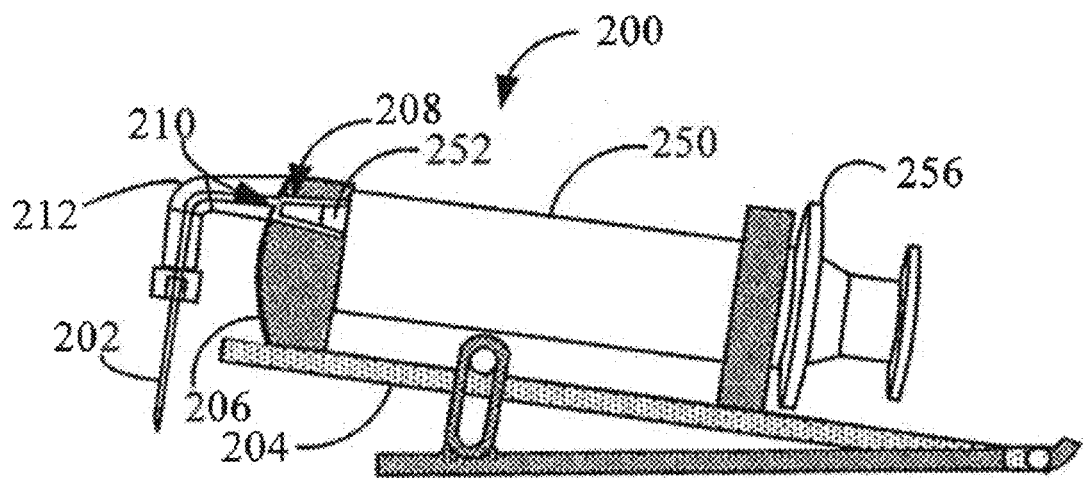
FIGS. 2A and 2B are side view simplified illustrations of optional exemplary embodiments of a modular patch type self-injector.
Figure 2B:
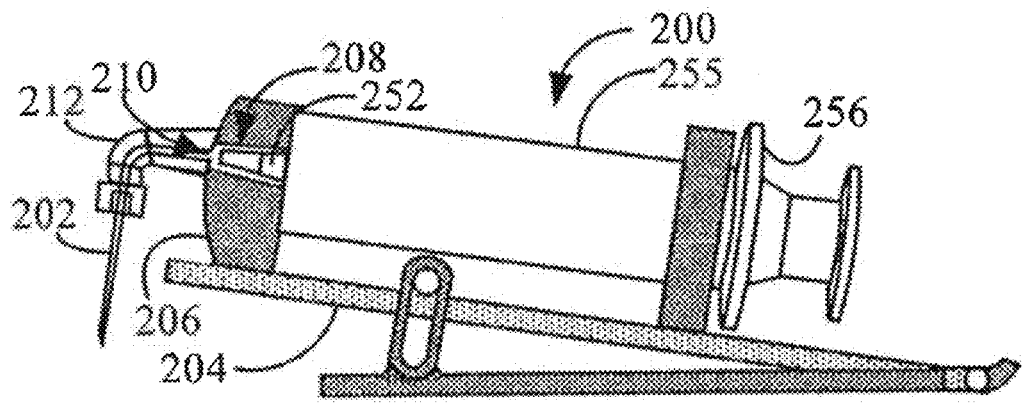

Reference is now made to FIGS. 2A, 2B and 2C, collectively referred to as FIG. 2, which are side view simplified illustrations of optional exemplary embodiments of a modular patch type self-injector. As shown in FIG. 2, a self-injector 200 may be sized and fitted to accommodate variable types and sizes of fluid reservoirs. As in the example of FIG. 1, in some embodiments, auto-injector 200 comprises a bent needle 202, e.g., bent at a 90 degree angle. As explained in greater detail elsewhere in the disclosure, in some embodiments, self-injector 200 comprises a support plate 204 and at least a needle 202-bearing portion 206. In some embodiments, needle-bearing portion 206 comprises at least a bore 208 sized and fitted to accommodate a fluid reservoir 250/255 tip 252. In some embodiments, bore 208 comprises an aperture 210 leading to the bent portion 212 of needle 202. In some embodiments, at least a portion of needle 202 sealingly extends through aperture 210 and into bore 208. In some embodiments, needle-bearing portion 206 is fixed on support plate 204.

In some embodiments, shown in FIG. 2A, bore 208 is disposed eccentrically within needle-bearing portion 206 to accommodate an eccentric tip fluid reservoir. In some embodiments, shown in FIG. 2B, bore 208 is disposed centrally within needle-bearing portion 206 to accommodate a regular (central) tip fluid reservoir.

Optional Examples of Injector-Fluid Reservoir Couplings

Commonly used fluid reservoir tips include slip or push on tips and Luer lock type tips. Plastic fluid reservoirs comprise plastic tips of both types whereas glass fluid reservoir tips are commonly made of metal. Some glass fluid reservoirs comprise glass slip-on type tips. The commonly used fluid reservoir-needle coupling practice attempts to maintain a sterile injectable passageway however this may be challenging at times. The common practice is to store both fluid reservoirs and needles each in a sterile pouch to limit their exposure time to the environment from the moment of removal from the pouch until the moment of injection. This practice is not practical when it comes to self-injectors and especially patch-type self-injectors.

Slip/Push-on Type

Figure 3A:
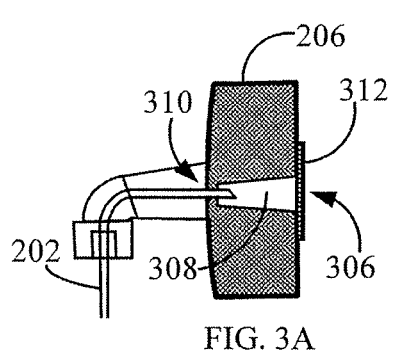
FIGS. 3A-3P are cross-section section and perspective view simplified illustrations of exemplary embodiments of injector-fluid reservoir couplings.
Figure 3B:
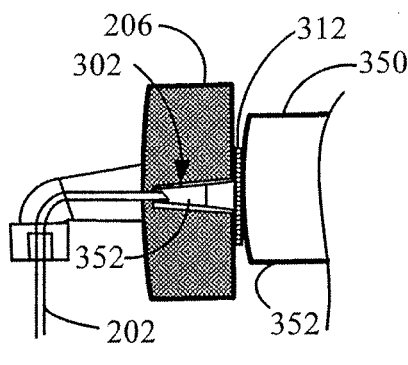
Figure 3C:
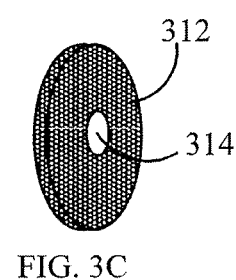
Figure 3D:
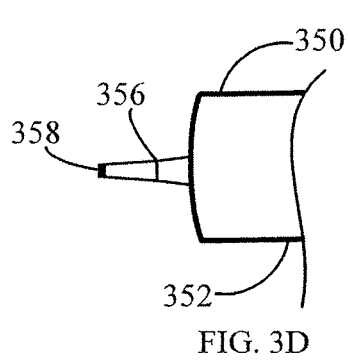
Figure 3E:
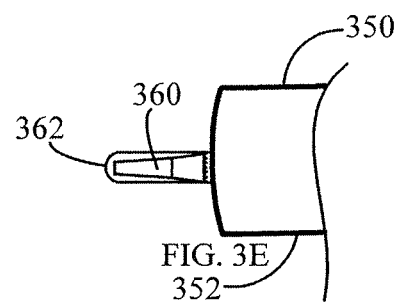
Figure 3F:
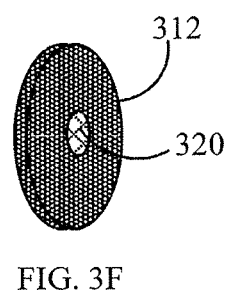
Figure 3G:
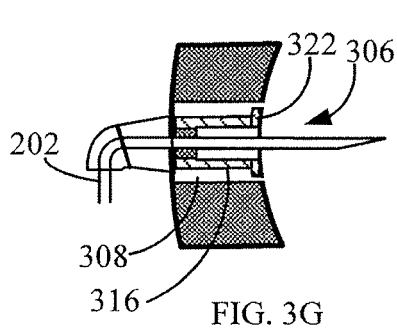
Figure 3H:
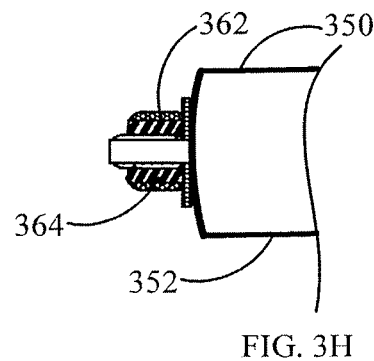
Figure 3I:
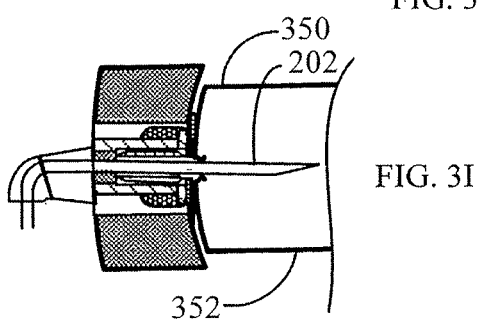
Figure 3J:
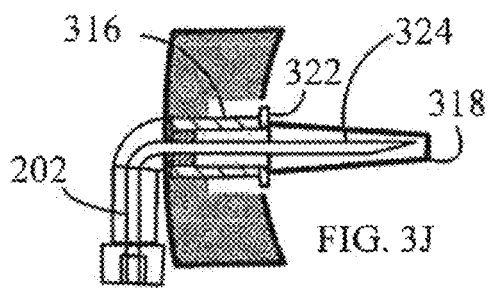
Figure 3L:
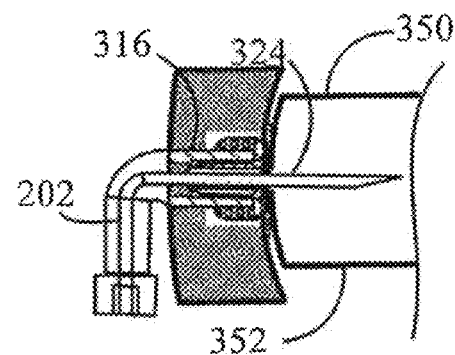
Figure 3K:
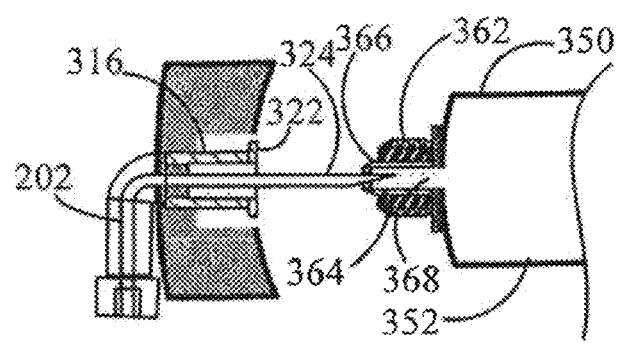
Figure 3N:
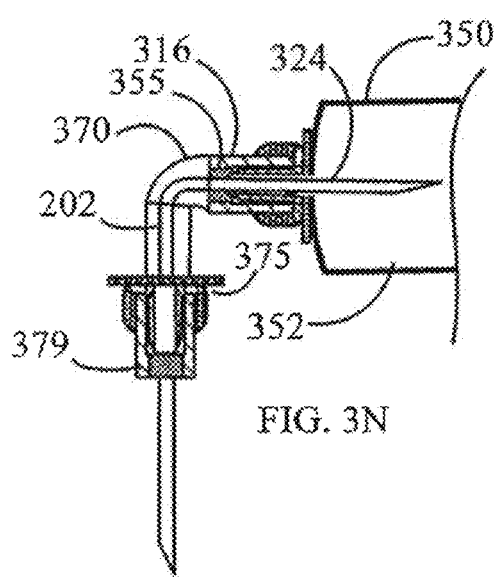
Figure 3M:
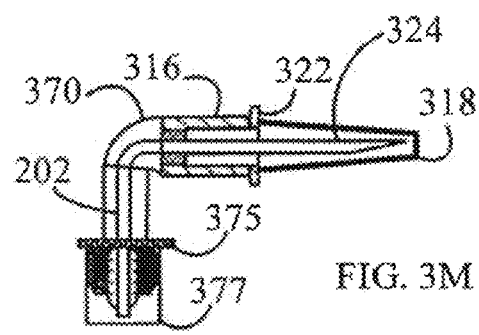
Figure 3O:
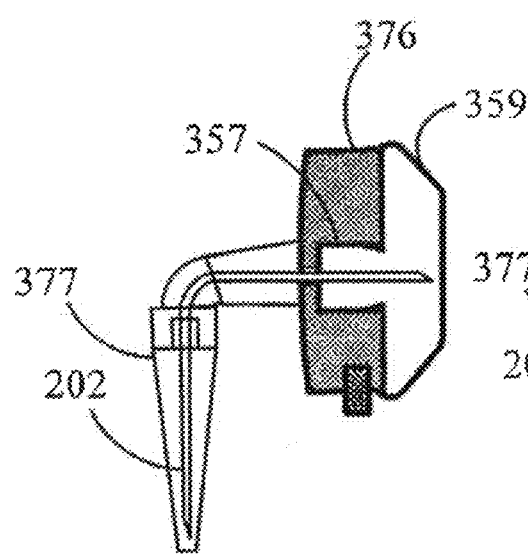
Figure 3P:
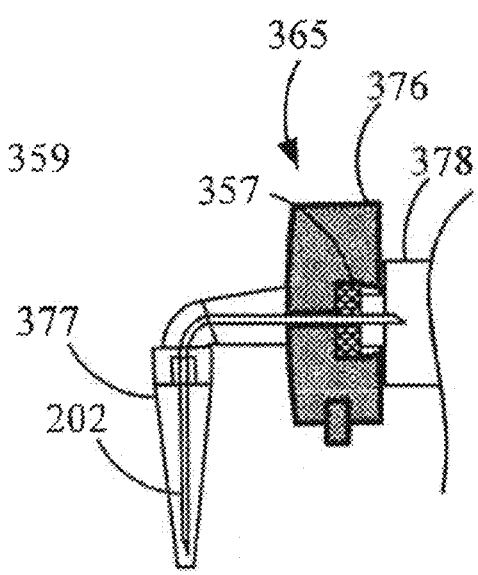

Reference is now made to FIGS. 3A-3P, collectively referred to as FIG. 3, which are cross-section section and perspective view simplified illustrations of exemplary embodiments of injector-fluid reservoir couplings. The exemplary embodiments of FIGS. 3A-3L depict one or more adaptors that couple needle 202 to one or more various fluid reservoir tip types. For example, FIG. 3A, illustrates needle-bearing portion 206 comprising an adaptor 302 sized and fitted for coupling needle 202 to a slip or push-on type fluid reservoir tip 352. A centrally disposed bore 308 opens on one side to an opening 306 facing a fluid reservoir to receive a fluid reservoir tip and ends on the opposite side at an aperture 310 on the opposite side sized to sealingly accommodate at least a portion of needle 202. Optionally, in some embodiments, bore 308 comprises cone geometry. In some embodiments, bore 308 comprises cylinder geometry. Optionally and as also shown in FIG. 3C, in some embodiments, needle-bearing portion 206 may further comprise a resilient fitting 312 attached adhesively or by any other suitable method over opening 306. In some embodiments, fitting 312 may comprise an aperture 314 sized to accommodate a correspondingly sized slide-on type fluid reservoir tip. In some embodiments, when at least a portion of a fluid reservoir 350 is urged against the resilient fitting when locked into place in the injector, resilient fitting 312 stops possible leaks from the fluid reservoir tip-needle coupling.

In some embodiments, fitting 312 may be made of a resilient type suitable material, e.g., Silicone to act as a seal and seal opening 306 when a fluid reservoir barrel 352 is urged against needle-bearing portion 206 as shown in FIG. 3B.

As illustrated in FIGS. 3A and 3B, in some embodiments, end of needle 316 may at least partially extend into bore 308 and into a lumen of a fluid reservoir tip 354 when a fluid reservoir 350 is coupled to the self-injector. As shown in FIGS. 3D and 3E, tips of a fluid reservoir 350 may be sealed for sterility. For example, an opening of a fluid reservoir tip 356 (FIG. 3D) may be sealed by a membrane 358, or, alternatively, a fluid reservoir tip 360 (FIG. 3E) may be covered by a protective sheath 362. In some embodiments, when coupled to a fluid reservoir 350, end 316 of needle 202 extending into bore 308 is configured to break most types of fluid reservoir tip seals protecting sterility of the injectable inside fluid reservoir 350. Ion some embodiments, and shown in FIG. 3F, fitting 312 aperture 314 may be sealed by a membranous seal 320. In some embodiments, when self-injector 200 is coupled to a fluid reservoir 350, a tip 356/360 of fluid reservoir 350 may break membranous seal 320.

Luer-Lock Type

Referring now to FIGS. 3G-3I which illustrate self-injector 200 comprising bent needle 202 and Luer-lock coupling 316 sized and fitted to receive a fluid reservoir 350 with a male Luer-lock type tip 362. In some embodiments, Luer-lock coupling 316 comprises a cylinder 35 sealingly coupled at one end to needle 202 and injector 200 and comprising a tabbed rim 322 on the opposite end that opens toward bore 308 opening 306. In some embodiments, tabbed rim 322 is configured to thread into a sleeve 364 on a male Leur-lock fluid reservoir tip 362. FIG. 3I shows Luer-lock coupling 316 and Luer-lock type fluid reservoir 350 tip 362 in a fully mated configuration.

The exemplary embodiment depicted in FIGS. 3J-3L illustrates a Luer lock coupling system similar to that described elsewhere in the disclosure. Optionally, in some embodiments and as shown in FIG. 3J, end 324 of bent needle 202 extending beyond Luer-lock coupling 316 tabbed rim 322 comprises a protective sheath 318 configured to maintain sterility needle end 324. In some embodiments, protective sheath 318 is made of a pliable membranous material e.g., rubber, polyurethane or any other suitable material. In some embodiments, when mated as shown in FIG. 3K, a rim 366 of male Luer lock fluid reservoir 350 tip 362 urges protective sheath 318 against needle end 324. In some embodiments and as shown in FIG. 3K, needle end 324 breaks protective sheath 318 as it enters into the lumen 368 of fluid reservoir Luer lock tip 362. FIG. 3L shows Luer-lock coupling 316 and Luer-lock type fluid reservoir 350 tip 362 in a fully mated configuration. Additionally and optionally, in some embodiments, fluid reservoir male Luer lock tip 316 comprises a seal similar to seal 358 of fluid reservoir tip 356.

In some embodiments and as shown in FIGS. 3M and 3N, self-injector may be comprise a bent needle adaptor 370 comprising a fluid reservoir coupling similar to the examples described elsewhere in the disclosure and a second coupling 375 at a second end of the adaptor 370. In the example depicted ion FIGS. 3M and 3N second coupling 375 comprises a Leur lock tip. A cover 377 protects second coupling 375 from the environment and maintains the sterility of needle adaptor 370. In some embodiments, adapter 370 provides the freedom to couple a standard needle 379 to self-injector 200. In the exemplary embodiment shown in FIG. 3N, protective cap 377 has been removed and a Leur lock tip needle 379 is coupled to needle adaptor 370 and fluid reservoir 350.

As shown in FIGS. 3O and 3P, an exemplary embodiment of bent needle adaptor 376 comprises a vial adaptor 357 such as, for example a Medimop Medical Projects Ltd. vial adaptor described in U.S. Pat. No. 7,326,194. In some embodiments, bent needle adaptor 376 comprises a sterile cover 359. In some embodiments, bent needle adaptor 376 comprises needle cap 377. Optionally and alternatively and as shown in FIG. 3P, bent needle adaptor 376 may be attached to an empty vial 378 to form a single non-sterile self-injector cartridge unit 365. In some embodiments, cartridge unit 365 can then be sterilized and filled with an injectable.

Optional Examples of Fasteners and Fittings

An aspect of some embodiments of the invention relates to a self-injector comprising a modular fluid reservoir-injector coupling system. Self-injectors and specifically patch self-injectors are designed to avoid movement of the injection needle in the tissue during the injection process and thus to minimize pain associated with the injection. This is achieved by various coupling methods that fixedly attach the injection needle and/or the fluid reservoir cartridge to the self-injector housing.

Figure 4A:
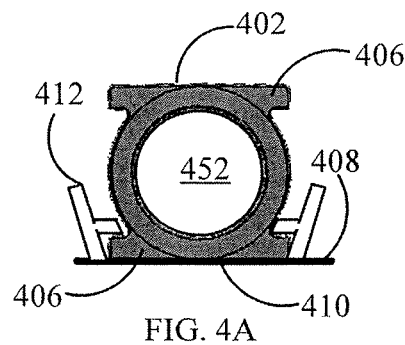
FIGS. 4A-4H are plan and perspective view simplified illustration of exemplary embodiments of a modular fluid reservoir-injector coupling system.
Figure 4H:
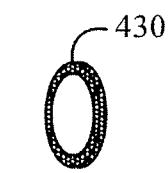
Figure 4B:
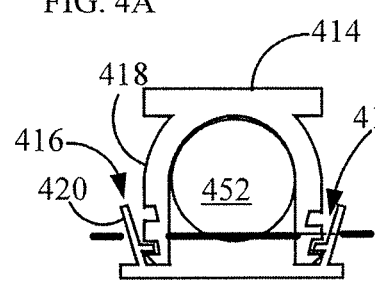
Figure 4C:
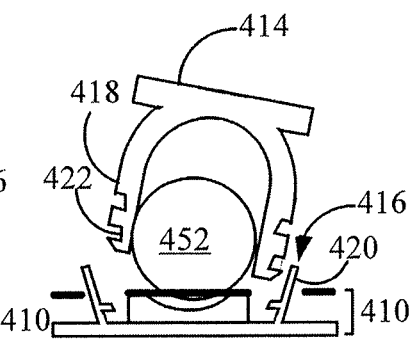

Reference is now made to FIGS. 4A-4H, collectively referred to as FIG. 4, which are plan and perspective view simplified illustration of exemplary embodiments of a modular fluid reservoir-injector coupling system. In the examples depicted in FIG. 4, self-injector 200 comprises one or more fasteners 402, sized and fitted to accommodate at least a barrel 452 or a finger flange 454 of a fluid reservoir 450. In some embodiments and as shown in FIGS. 4A and 4B, injector 200 comprises one or more fasteners configured to couple variable types and sizes of fluid reservoirs to self-injector 200. As shown in FIG. 4A, in some embodiments, a fastener 404 comprises ring geometry sized and fitted to slide onto a fluid reservoir barrel of a corresponding diameter. In some embodiments, fastener 404 further comprises at least one protrusion 406 extending from the periphery of fastener 404. In the exemplary embodiment depicted in FIG. 4A protrusion 406 extends tangentially from the ring of fastener 404, however protrusion 406 may extend radially or in any other suitable geometric configuration. In some embodiments, protrusion 406 is oriented parallel at least to a surface 408 of a support plate 410. In the exemplary embodiment illustrated in FIG. 4A, at least one protrusion 406 is fixedly coupled to the support plate 410 by at least one retention member. In the example shown in FIG. 4A, the attachment member comprises a retention cantilever 412. In some embodiments, retention lever 412 are elastic and/or comprise at least an elastic coupling to support plate 410. However, the attachment member may comprise any type of suitable attachment mechanism. In some embodiments, retention cantilever 412 is configured to releasably couple fastener 404 protrusion 406 to support plate. FIGS. 4B and 4C illustrate an exemplary embodiment in which fastener 414 comprises an inverted U geometry. In some embodiments, support plate 410 a plurality of notches 416 configured to accommodate legs 418 of fastener 414. In some embodiments, support plate 410 notches 416 comprise retention cantilevers 420 configured to releasably couple fastener 414 to support plate by fitting into one or more corresponding recesses 422 in legs 418. Optionally, a plurality of recesses 422 supports adjustment of the internal radius of fastener 414 by adjusting the depth of insertion of fastener 414 one or more legs 418 into support plate 410. Thus, a plurality of recesses 422 renders fastener 414 to be configured to size and fit a variety of fluid reservoir sizes.

Figure 4D:
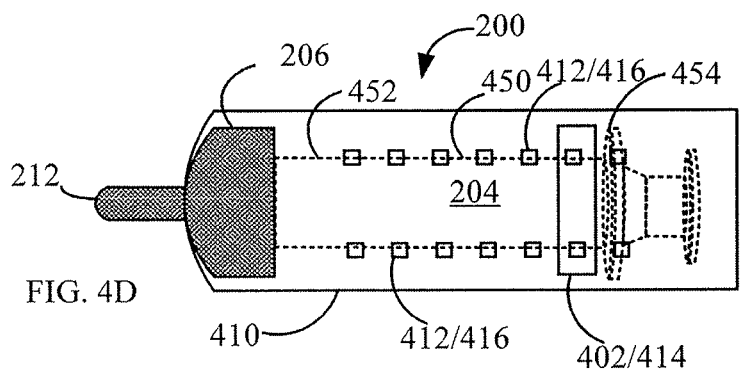

As shown in FIG. 4D, in some embodiments, support plate 410 comprises a plurality of attachment points 412/416 distributed in a fashion that allows fasteners 402/414/424 to be coupled to support plate 410 at varying distances from needle portion 206 to accommodate fluid reservoirs of varying lengths. In some embodiments, attachment points 412/416 optionally comprise cantilevers 420 of the type shown in FIG. 4A. In some embodiments, attachment points 412/416 optionally comprise notches 416 and retention cantilevers 420 configured to releasably couple fasteners of the type depicted in FIGS. 4B and 4C. In some embodiments, attachment points 412/416 optionally comprise sliding hinges and retention levers in a configuration shown in FIGS. 4E and 4F. Additionally and optionally, attachment points 412/416 may comprise any similar suitable attachment mechanism other than the exemplary embodiments described herein.

Figure 4E:
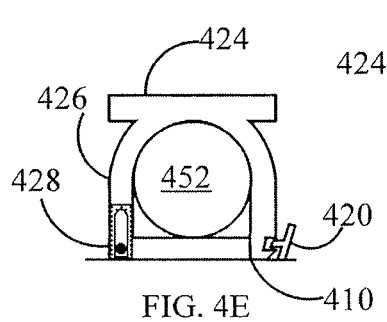
Figure 4F:
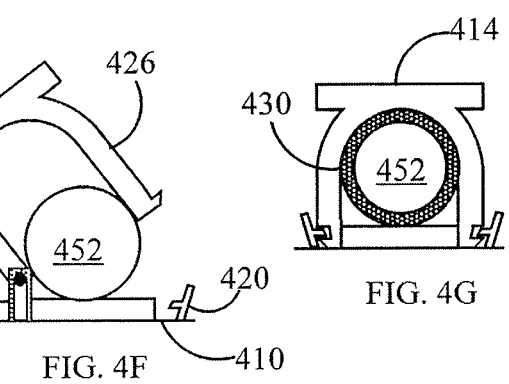

FIGS. 4E and 4F illustrate an exemplary embodiment in which fastener 424 comprises a hinged inverted U geometry.

In the example in FIGS. 4E and 4F one leg 426 comprises a sliding hinge 428 configured to form a large gap when open to release or receive a fluid reservoir barrel 452. In the closed configuration shown in FIG. 4E, fastener 424 non-hinged leg 426 is locked in place by a retention cantilever 420.

Figure 4G:
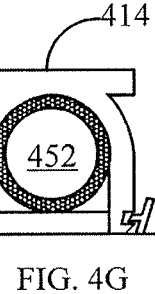

In some embodiments, at least one of fasteners 402/414/424 comprises the same size to fit onto the same support plate 410. In some embodiments and as shown in FIGS. 4G and 4H, fasteners 402/414/424 are fitted with one or more ring geometry fittings 430 (FIG. 4H) at various diameters sized and fitted to a corresponding diameter of a specific fluid reservoir barrel. In some embodiments, fittings 430 are configured to slide onto a barrel 452 of a fluid reservoir 450 and provide sufficient friction when a fastener, e.g. fasteners 414/424 is in the closed configuration to prevent axial slippage and movement of fluid reservoir barrel 452 in respect to support plate 410.

FIGS. 4G and 4H depict a fastener of the type illustrated in FIGS. 4B and 4C, however fittings 430 may be fitted in any one of the fasteners described herein or any other similar type of fastener.

Optional Examples of Adaptor-Fluid Reservoir Couplings and Fasteners Positioning In order to secure fixed coupling of a fluid reservoir to a self-injector, fasteners such as fasteners 420/414/424 need to be adjusted to a length of a fluid reservoir barrel in addition to fixing the fluid reservoir to a surface such as support plate 410. In most cases this can be achieved by sliding the fastener along the fluid reservoir barrel as described elsewhere in the disclosure and/or couple a fastener to a finger flange of the fluid reservoir. The structure of modular support plate 410 described elsewhere in the disclosure allows for positioning a fastener at almost any desired location when fitted to a fluid reservoir barrel or finger flange. Reference is now made to FIGS. 5A-5G, which are part sectional side view simplified illustrations of positioning of fasteners coupling a fluid reservoir to a self-injector.

Figure 5A:
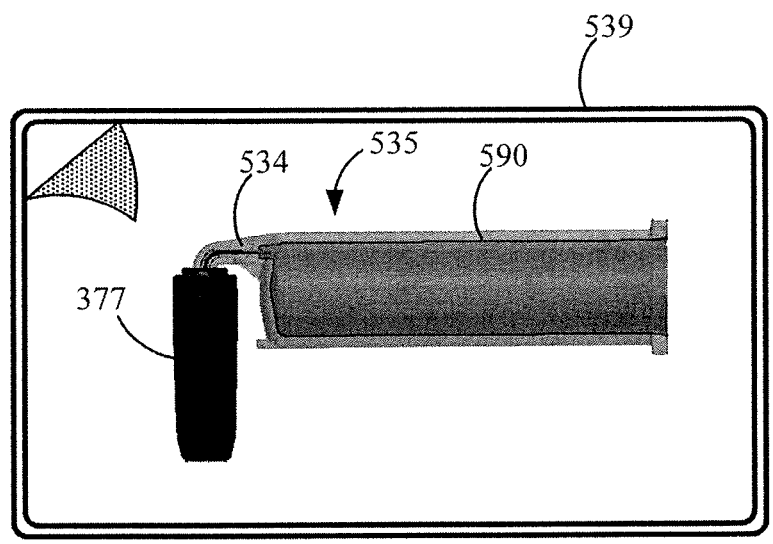
Figure 5B:
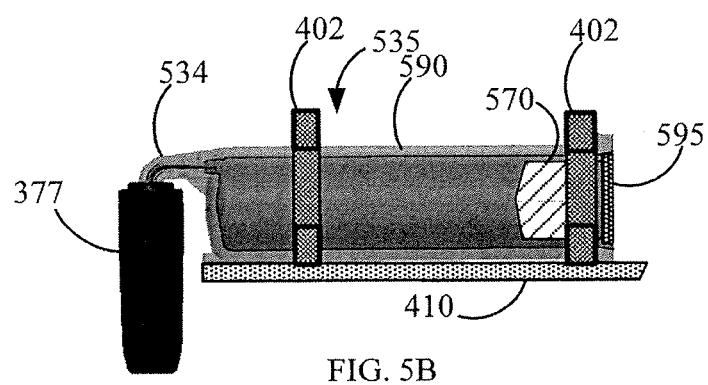

In the exemplary embodiment depicted in FIG. 5A an empty fluid reservoir 590 is coupled to a needle-bearing portion 534 to form a single integral self-injector cartridge unit 535. In some embodiments, cartridge unit 535 is sterile. In some embodiments, cartridge unit 535 is non-sterile. In some embodiments, cartridge unit 535 is sterilized, filled with an injectable in a sterile fashion and provided sterile, sealed and ready for use. As shown in the exemplary embodiments illustrated in FIG. 5B, a sterilely pre-filled cartridge unit 535 is coupled to support plate 410 by one or more fasteners 402 (FIG. 4A). In some embodiments, cartridge unit 535 comprises a plunger 570 and is sealed after filling for sterility with a seal 595. In some embodiments, cartridge unit 535 is delivered unsterile for sterilization and filling in an envelope e.g., a plastic blister 539. As shown in FIG. 5C, a fluid reservoir 550 e.g., 20 cc fluid reservoir, comprising a slip-on tip is mounted onto self-injector 500. In the exemplary embodiment shown in FIG. 5C tip 502 is shown to be inserted into a needle-bearing portion 506 in a fashion described elsewhere in the disclosure and will not be repeated. In the exemplary embodiment depicted in FIG. 5C, needle-bearing portion 506 comprises a coupling similar to that of fastener 504 and is reversibly coupled to support plate 410. In some embodiments, one or more fasteners 504 of a form and function of which is described elsewhere in the disclosure and will not be repeated are positioned along barrel 452 at least one of which abutting a finger flange 454 coupling a barrel 452 of fluid reservoir 450 to support plate 410. In some embodiments, when closed, fastener 504 provides sufficient friction against barrel 452 to prevent axial slippage and movement of barrel 452 in respect to support plate 410. Alternatively and optionally, in some embodiments, a fitting of a type described elsewhere in the disclosure may be fitted inside fastener 504 and provide sufficient friction against barrel 452 to prevent axial slippage and movement of barrel 452 in respect to support plate 410.

Alternatively and optionally and as shown in FIG. 5D, in some embodiments, a fastener 506 comprises a radial slot 508 along an internal wall 510 sized and fitted to accommodate a corresponding sized fluid reservoir finger flange 454. Alternatively and optionally and as shown in FIG. 5E, in some embodiments, a fastener of the type of fastener 504 comprises a fitting 512 fitted inside fastener 504 comprising a radial slot 514 along an internal wall of fitting 512 is sized and fitted to accommodate a corresponding sized fluid reservoir finger flange 454. In some embodiments, fitting 512 provides sufficient friction against finger flange 454 to prevent axial slippage and movement of barrel 452 in respect to support plate 410. In FIG. 5D a fluid reservoir plunger has been replaced with a plunger 570 configured to be driven by a self-injector 500 plunger driving system (not shown).

Alternatively and optionally, modular fluid reservoir-injector coupling system is shown in FIG. 5F coupling a small sized fluid reservoir 555 e.g., 5 cc fluid reservoir to self-injector 500. fluid reservoir 555 slip-on tip is shown to be inserted into a needle-bearing portion 506 in a fashion described elsewhere in the disclosure and will not be repeated. In some embodiments, one or more fasteners 504 of a form and function of which is described elsewhere in the disclosure and will not be repeated are positioned along barrel 552 at least one of which abutting a finger flange 554 coupling a barrel 552 of fluid reservoir 555 to support plate 410. In some embodiments, when closed, fastener 504 provides sufficient friction against barrel 552 to prevent axial slippage and movement of barrel 552 in respect to support plate 410. Alternatively and optionally, in some embodiments, a fitting 430 of a type described elsewhere in the disclosure may be fitted inside fastener 504 and provide sufficient friction against barrel 552 to prevent axial slippage and movement of barrel 552 in respect to support plate 410.

Figure 6:
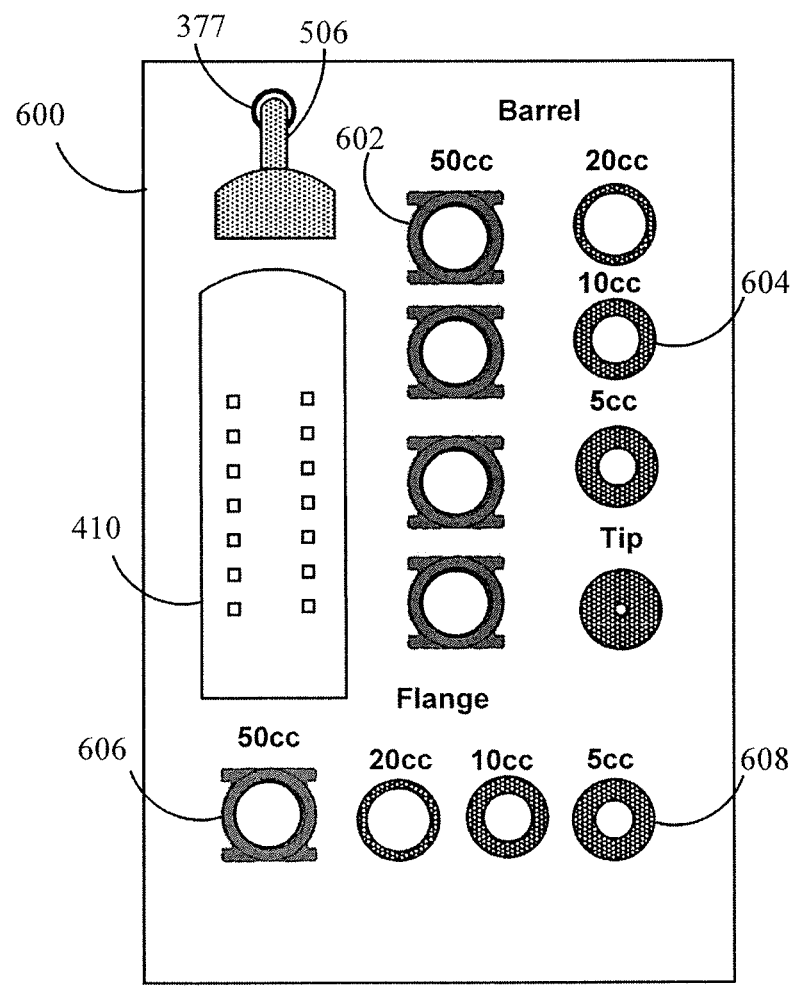
FIG. 6 is a plan view simplified illustration of a home kit for self-injection.

In the embodiment shown in FIG. 5F, a fitting 512 fitted inside fastener 504 is sized and fitted to accommodate corresponding sized fluid reservoir finger flange 554. As shown in FIG. 5G, needle-bearing portion 506 comprises a coupling 537 to support plate similar to that of fasteners 504 or any type of fastener coupling described elsewhere in the disclosure and is reversibly coupled to support plate 410. As shown in FIG. 5G, in some embodiments, a finger-flangeless fluid reservoir 590 is sealingly attached to needle-bearing portion 506. In the exemplary embodiment depicted in FIG. 5G, fluid reservoir 590 is a pre-filled vial attached to needle-bearing portion 506 and fitted with a fastener 402 (FIG. 4C) to be mounted onto support plate 410 as explained elsewhere in the disclosure. In some embodiments, needle-bearing portion 506 comprises a needle 202 protective cap 377. In some embodiments, fluid reservoir 590 is sealed for sterility with a seal 595. In some embodiments, pre-filled fluid reservoir 590 attached to needle-bearing portion 506 is delivered in an envelope e.g., a plastic blister 539. Reference is now made to FIG. 6, which is a plan view simplified illustration of a home kit for self-injection. As shown in FIG. 6, in some embodiments a kit 600 comprises a self-injector, represented in FIG. 6 by a modular support plate 410, a plurality of fasteners 602 and a variety of fittings 604 comprising various internal diameters.

Additionally and optionally, in some embodiments kit 600 may comprise markings that assist a user to select the correct fastener or fitting for the corresponding selected fluid reservoir. For example, in the exemplary embodiment depicted in FIG. 6, for a selected 50 cc fluid reservoir the user may select only fasteners to sufficiently couple the fluid reservoir to the self-injector. For a smaller sized fluid reservoir, e.g., 10 cc fluid reservoir the user may select a fastener and a fitting marked "10 cc" to be inserted into the fastener. In some embodiments, kit 600 comprises clearly marked indicators as to fitting sizes and types of fasteners and fittings e.g., "5 cc", "10 cc", "20 cc", "50 cc", "tip", "Flange", etc.

In some embodiments, a user would use kit 600 to couple a fluid reservoir to a self-injector by removing the self-injector from the kit and opening a cover to expose support plate 410. In some embodiments, the method further comprises coupling needle bearing portion 506 to the fluid reservoir. In some embodiments, needle bearing portion 506 comprises a needle protective cap 377. In some embodiments, the method further comprises selecting one or more fasteners 602 and sliding one or more fasteners on a barrel 452/552 of a fluid reservoir. Alternatively and optionally the method comprises coupling one or more fasteners 602 to support plate 410. Optionally, the method comprises inserting one or more fittings 604 into one or more fasteners 602 before sliding onto a barrel 452/552 of a fluid reservoir. 1o Additionally and optionally, the method comprises selecting a finger flange fastener 606 and coupling the fluid reservoir flange to support plate 410. Optionally, the method comprises inserting one or more finger flange fittings 608 into one or more fasteners 602 before coupling the fluid reservoir flange to support plate 410. Optionally, the method comprises selecting at least one attachment points 412/416 and attaching a fastener 604/606 to the selected attachment points 412/416.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding to errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An add-on for a self-injector comprising:
    an adaptor comprising a first coupling at a first end of the adaptor sized and shaped to couple said adaptor to a fluid reservoir, a second coupling at a second end of the adaptor, a first body portion extending from said first coupling, said first body portion being elongate along a first axis, a second body portion extending from said second coupling, said second body portion being elongate along a second axis angularly offset from said first axis, and an elbow portion connecting said first and second body portions;
    a rigid and bent fluid path having a first end configured to penetrate tissue and a second end coupled to said adaptor; and
    a needle protective cap covering said first end of said fluid path and a protective sheath covering said second end of said fluid path,
        wherein said add-on is coupled to said fluid reservoir such that said second end of said fluid path is in fluid communication with said fluid reservoir, and wherein said add-on coupled to said fluid reservoir forms an integral self-injector cartridge unit configured to be sterilized and filled with an injectable.

2. The add-on according to claim 1, wherein said fluid path is bent at a 90 degree angle.

3. The add-on according to claim 1, further comprising at least one fastener sized and fitted to couple a body of said fluid reservoir to a self-injector.

4. The add-on according to claim 3, an internal diameter of the at least one fastener being adjustable;
wherein said adaptor and said fastener are configured to couple to said self-injector at least one of a plurality of reservoirs having different sizes and tip types.

5. The add-on according to claim 4, wherein the distance between said adaptor and said fastener is adjustable.

6. The add-on according to claim 4, wherein said plurality of reservoirs include fluid reservoirs.

7. The add-on according to claim 3, wherein the add-on further comprises a fitting sized and shaped to fit along the inner circumference of said at least one fastener.

8. The add-on according to claim 7, wherein said fitting reduces the inner diameter of said at least one fastener.

9. The add-on according to claim 3, wherein at least a portion of said at least one fastener is made of a plastic material.

10. The add-on according to claim 1, wherein said second coupling is sized and shaped to couple said bent fluid path to said adaptor and secure sterile fluid communication in-between.

11. The add-on according to claim 1, wherein said bent fluid path comprises a hollow needle.

12. The add-on according to claim 1, wherein said reservoir is a prefilled cartridge.

13. The add-on according to claim 1, wherein said reservoir is a syringe.

14. The add-on according to claim 1, wherein said reservoir is a vial.

15. The add-on according to claim 1, wherein at least a portion of said reservoir is made of glass.

16. The add-on according to claim 1, wherein at least a portion of said reservoir is made of a plastic material.

17. The add-on according to claim 1, wherein said add-on is sterilizable en bloc.

18. The add-on according to claim 1, wherein said at least one coupling is a vial adaptor.

19. The add-on according to claim 1, wherein said second coupling is sized and shaped to couple said add-on to a self-injector.

20. The add-on according to claim 1, wherein said first coupling is a Luer lock coupling.

21. The add-on according to claim 1, wherein said at least one coupling is a slide-on fluid reservoir coupling.

22. A self-injector coupling system comprising
a self-injector comprising a support plate with a plurality of attachment points;
the add-on according to claim 1; and
at least one fastener sized and fitted to couple to a body of said fluid reservoir and to at least one of said attachment points; and
a retention cantilever configured to releasably couple said at least one fastener to said support plate.

23. The system according to claim 22, wherein said adaptor is sized and fitted to couple to at least one of said attachment points.

24. The system according to claim 22, wherein said attachment points are distributed on said support plate at varying distances from said adaptor.

25. The system according to claim 22, wherein said varying distances correspond to varying lengths of said fluid reservoir.

26. A self-injector kit, comprising
at least one self-injector comprising a support plate with a plurality of attachment points;
a plurality of the add-ons according to claim 1; and
a plurality of fasteners sized and fitted to couple to at least one diameter of a body of said fluid reservoir and to at least one of said attachment points;
a plurality of retention cantilevers configured to releasably couple said plurality of fasteners to said support plate.

27. The kit according to claim 26, wherein at least one of said adaptors is sterile.

28. A method of assembling an add-on for a self-injector comprising:
selecting an empty fluid reservoir;
forming the integral self-injector cartridge unit by coupling at least a tip of said fluid reservoir to the add-on according to claim 1; and
establishing fluid communication between said fluid reservoir and said bent fluid path.

29. The method according to claim 28, further comprising sterilizing said cartridge unit;
filling said fluid reservoir with a sterile injectable;
inserting a plunger into an non-bent fluid path end of said fluid reservoir; and
sterilely sealing said end of said fluid reservoir.

30. The method according to claim 28, further comprising selecting at least one fastener and coupling said fastener to a body of said fluid reservoir; and
coupling said fastener to at least one corresponding attachment point on said injector.

31. A method of coupling an add-on for a self-injector to a fluid reservoir comprising:
selecting a fluid reservoir;
coupling at least a tip of said fluid reservoir to the add-on according to claim 1; and
establishing sterile communication between said fluid reservoir and said bent fluid path.

32. The method according to claim 31, further comprising selecting at least one fastener and coupling said fastener to a body of said fluid reservoir; and
coupling said fastener to at least one corresponding attachment point on said injector.

33. The add-on according to claim 1, wherein said second coupling is a Luer lock coupling.

* * * * *